US012806335B2

(12) United States Patent
Reeves

(10) Patent No.: US 12,806,335 B2
(45) Date of Patent: Nov. 24, 2026

(54) AUTOMATIC FLUID PRODUCT INJECTION DEVICE

(71) Applicant: APTAR FRANCE SAS, Le Neubourg (FR)

(72) Inventor: Sam Reeves, Bristol (GB)

(73) Assignee: APTAR FRANCE SAS, Le Neubourg (FR)

( * ) Notice: Subject to any disclaimer, the term of this patent is extended or adjusted under 35 U.S.C. 154(b) by 1525 days.

(21) Appl. No.: 16/604,254

(22) PCT Filed: Apr. 6, 2018

(86) PCT No.: PCT/FR2018/050859
§ 371 (c)(1),
(2) Date: Oct. 10, 2019

(87) PCT Pub. No.: WO2018/189459
PCT Pub. Date: Oct. 18, 2018

(65) Prior Publication Data
US 2020/0155758 A1 May 21, 2020

(30) Foreign Application Priority Data
Apr. 10, 2017 (FR) ....................................... 1753093

(51) Int. Cl.
*A61M 5/155* (2006.01)
*A61M 5/142* (2006.01)

(52) U.S. Cl.
CPC ........ *A61M 5/155* (2013.01); *A61M 5/14248* (2013.01); *A61M 2205/3653* (2013.01)

(58) Field of Classification Search
CPC ...... A61M 2205/3653; A61M 5/14248; A61M 5/14244; A61M 5/145; A61M 5/155
See application file for complete search history.

(56) References Cited

U.S. PATENT DOCUMENTS 4,070,859 A 1/1978 Sobecks
5,135,498 A * 8/1992 Kam .................. A61M 5/1483 128/DIG. 12

(Continued)

FOREIGN PATENT DOCUMENTS

WO 2008/057223 A2 5/2008

OTHER PUBLICATIONS

International Preliminary Report on Patentability and Written Opinion dated Oct. 24, 2019 from the International Bureau in counterpart International Application No. PCT/FR2018/050859.

(Continued)

*Primary Examiner* — Quynh-Nhu H. Vu
(74) *Attorney, Agent, or Firm* — Sughrue Mion, PLLC

(57) ABSTRACT

An automatic fluid injection device having a body fastened to a support for coming into contact with an injection zone, the body containing one or more fluid reservoirs each containing an injection piston; a needle assembly including an injection needle for penetrating into the injection zone; and an injection mechanism. The injection mechanism having an actuator cap containing an expandable material, and a heater mechanism for heating the expandable material, thus causing it to expand so as to move the piston in the reservoir, and thus inject the fluid into the injection zone through the injection needle. The expandable material has thermally expandable microspheres.

12 Claims, 6 Drawing Sheets

(56) References Cited

U.S. PATENT DOCUMENTS

| | | | | | |
|---|---|---|---|---|---|
| 5,222,362 | A * | 6/1993 | Maus | A61M 5/145 | 60/527 |
| 5,318,540 | A * | 6/1994 | Athayde | A61M 5/148 | 604/141 |
| 7,686,788 | B2 * | 3/2010 | Freyman | A61M 5/1483 | 604/181 |
| 2007/0066939 | A1 * | 3/2007 | Krulevitch | A61M 5/1452 | 604/152 |

OTHER PUBLICATIONS

International Search Report of PCT/FR2018/050859 dated Jul. 17, 2018 [PCT/ISA/210].

* cited by examiner

AUTOMATIC FLUID PRODUCT INJECTION DEVICE

CROSS REFERENCE TO RELATED APPLICATIONS

This application is a National Stage of International Application No. PCT/FR2018/050859, filed Apr. 6, 2018, claiming priority to French Patent Application No. 1753093, filed Apr. 10, 2017.

The present invention relates to an automatic fluid injection device.

Automatic fluid injection devices are well known. In particular, they include auto injectors in which the contents of a reservoir, generally a syringe, are automatically injected by means of an actuator system that generally includes a loaded spring, and that, on being triggering, moves a piston in the reservoir so as to inject the fluid.

Such prior-art devices can present problems, in particular when the volumes to be dispensed are large, when the fluid is relatively viscous, or when a plurality of fluids need to be combined in a single treatment.

Documents U.S. Pat. No. 5,222,362, WO 2008/057223, and U.S. Pat. No. 4,070,859 describe prior-art devices.

An object of the present invention is to provide an automatic injection device that does not have the above-mentioned drawbacks.

Another object of the present invention is to provide an automatic injection device that makes it possible to dispense fluid automatically, even at large volumes and/or high viscosities.

Another object of the present invention is to provide an automatic fluid injection device that is simple and inexpensive to manufacture and to assemble.

The present invention thus provides an automatic fluid injection device comprising: a body that is fastened to a support for coming into contact with an injection zone, said body containing one or more fluid reservoirs each containing an injection piston; a needle assembly including an injection needle for penetrating into the injection zone; and an injection mechanism; said injection mechanism comprising an actuator cap containing an expandable material, and heater means for heating said expandable material, thus causing it to expand so as to move said piston in said reservoir, and thus inject the fluid into said injection zone through said injection needle, said expandable material comprising thermally expandable microspheres.

Advantageously, said thermally expandable microspheres comprise hollow microscopic thermoplastic spheres encapsulating a hydrocarbon.

Advantageously, said hollow microscopic thermoplastic spheres, after heating to a temperature in the range 60° C. to 90° C., expand and are subjected to a transformation into a gas phase, making it possible for said thermally expandable microspheres to expand in the range five times to seventy times their original volume.

Advantageously, said device includes a priming assembly comprising a priming actuator and one or more priming needles for penetrating into the reservoir(s).

Advantageously, said support includes a sticker for fastening onto the injection zone.

Advantageously, each reservoir has a fluid content in the range 1 milliliters (mL) to 10 mL, advantageously about 3 mL.

Advantageously, said body includes a plurality of reservoirs, in particular three reservoirs.

Advantageously, the fluids contained in said reservoirs are dispensed simultaneously, being mixed together upstream of said injection needle.

Advantageously, the fluids contained in said reservoirs are dispensed successively.

Advantageously, said device includes power supply means, advantageously an optionally rechargeable battery.

These characteristics and advantages and others appear more clearly from the following detailed description, given by way of non-limiting example, and with reference to the accompanying drawings, in which.

The invention relates to an automatic injection device that is particularly adapted to dispense relatively large volumes of fluid, typically about a few milliliters, typically in the range 1 mL to 10 mL, e.g. 3 mL. The device of the invention is also adapted to dispense fluids that are relatively viscous.

The device is preferably disposable and can operate with the following operating steps:

1) the user removes the packaging and fastens the device on an injection zone, e.g. by means of a sticker provided for this purpose;

2) the user presses on an actuator button 200 so as to actuate the device, which serves in particular to prime the device, to insert the injection needle into the injection zone, to administer the fluid, and then to retract the injection needle;

3) the user is alerted when the process has ended, and detaches the appliance from the body and disposes of it.

Figure 1:
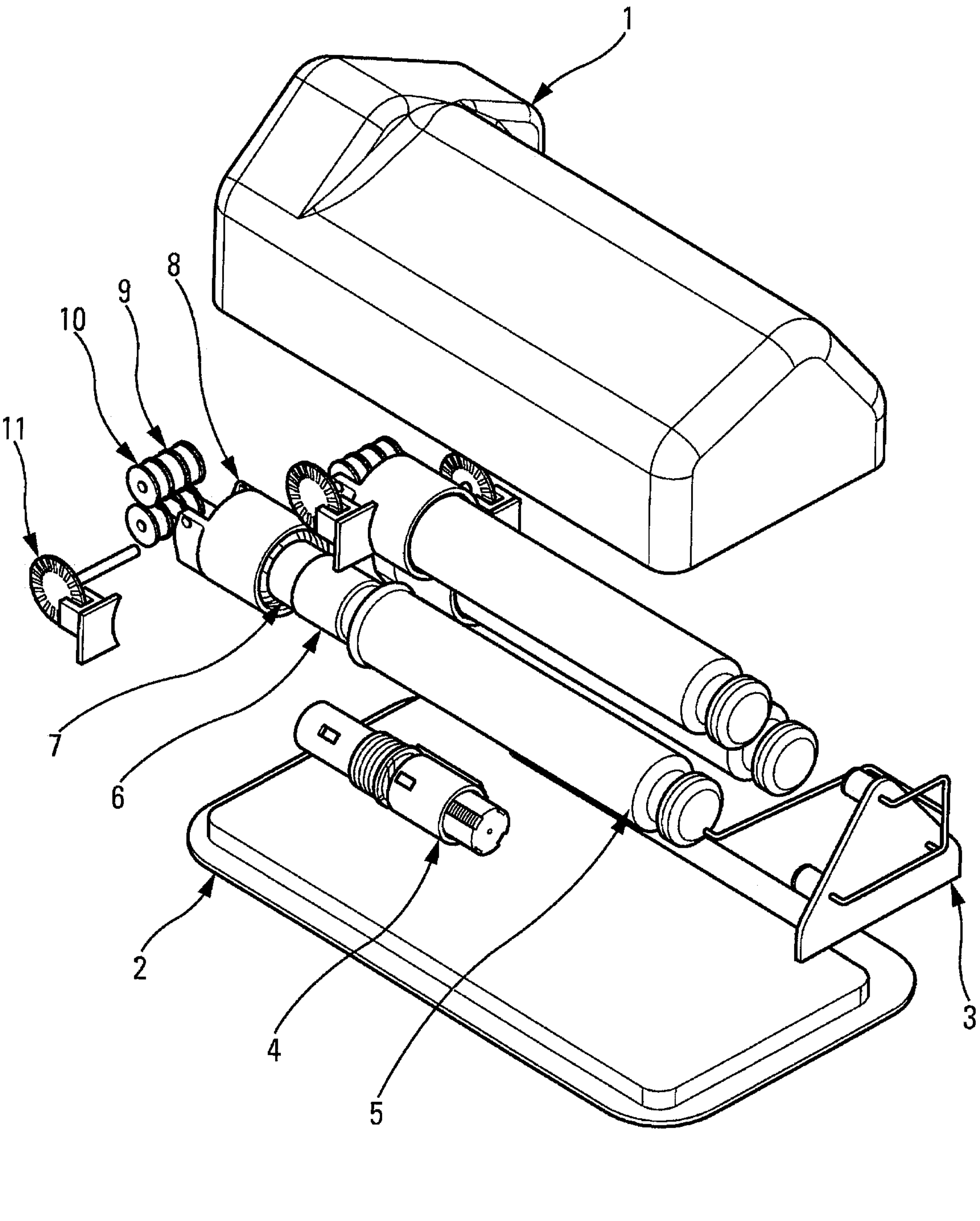
FIG. 1 is an exploded diagrammatic perspective view of an automatic injection device in an advantageous embodiment.

FIG. 1 shows an automatic injection device in an advantageous embodiment.

The device comprises: a body 1 that is fastened to a support 2 for coming into contact with the injection zone, said body containing one or more fluid reservoirs 5 each containing an injection piston 6; a priming assembly 3 comprising a priming actuator and one or more priming needles 31 for penetrating into the reservoir(s) 5; a needle assembly 4 including an injection needle 40 (not shown in FIG. 1) for penetrating into the injection zone; an injection mechanism 7-11; and power supply means (not shown).

By way of example, the power supply may be an optionally rechargeable battery.

In this embodiment, the injection mechanism is of the thermal type.

The embodiment of the system shows a set of three reservoirs 5 with a priming assembly 3 and a needle assembly 4.

Actuating the device gives rise to the following series of controlled internal processes:

1) Actuation of the priming assembly 3, that may also include an indicator mechanism (microswitch, etc.), in order to alert the priming controller that piercing of the membrane or of the reservoirs has terminated.

2) Insertion of the injection needle via an electronically-controlled mechanism; this system may also include an indicator for indicating, to the injection controller, when pricking has ended.

3) Triggering of the injection mechanism.

4) Retraction of the injection needle via the electronically-controlled mechanism, with an indicator mechanism (e.g. a microswitch, an open-loop timer) so as to indicate to the user (visually, e.g. via a diode, and/or audibly, e.g. via a sound signal) that the device may be removed from the body.

The above-described sequence might involve the presence of a small volume of air in the priming and needle assembles, and in particular in the priming and injection needles, in which circumstance the fluid would be injected into the sub-cutaneous tissue while the device is in use.

For applications in which such a volume of air, even very small, is not acceptable, the actuation sequence of the device may include the following additional step 1.1:

1.1) After priming and before inserting the injection needle into the injection zone, the injection mechanism is actuated early so as to dispense a small controlled volume of the fluid contained in the reservoir, so as to expel the air contained in the priming and needle assemblies.

Figure 2:
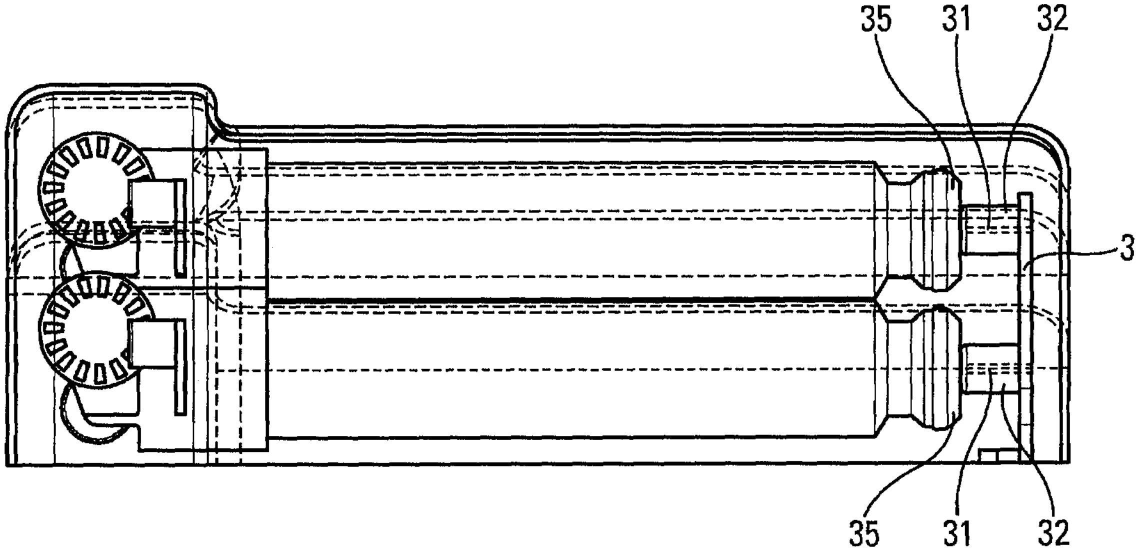
FIGS. 2 and 3 are diagrammatic side views of the FIG. 1 device, respectively before and after priming.
Figure 3:
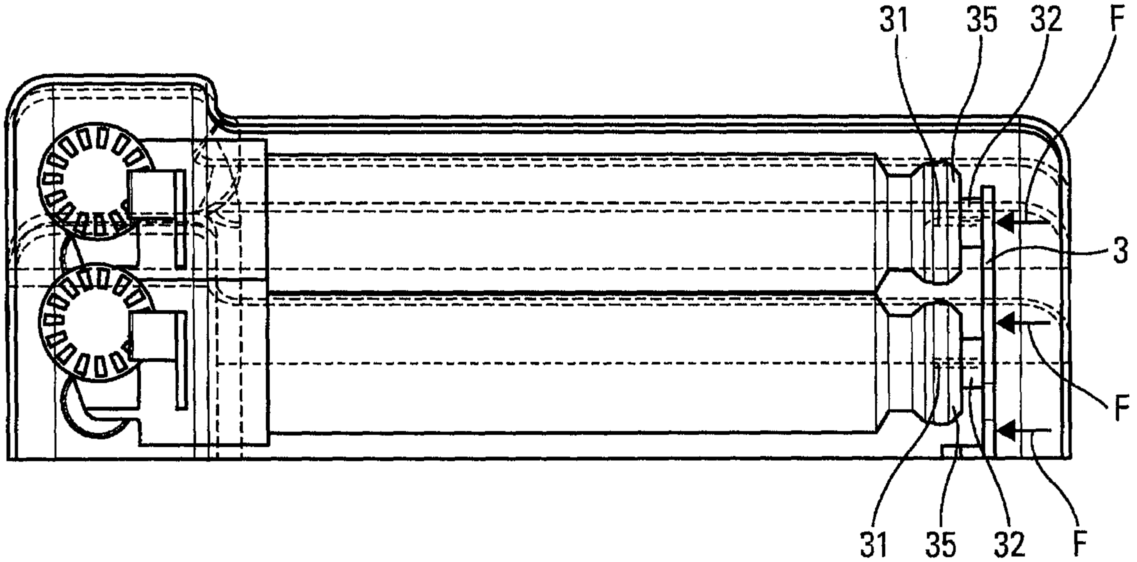
Figure 4:
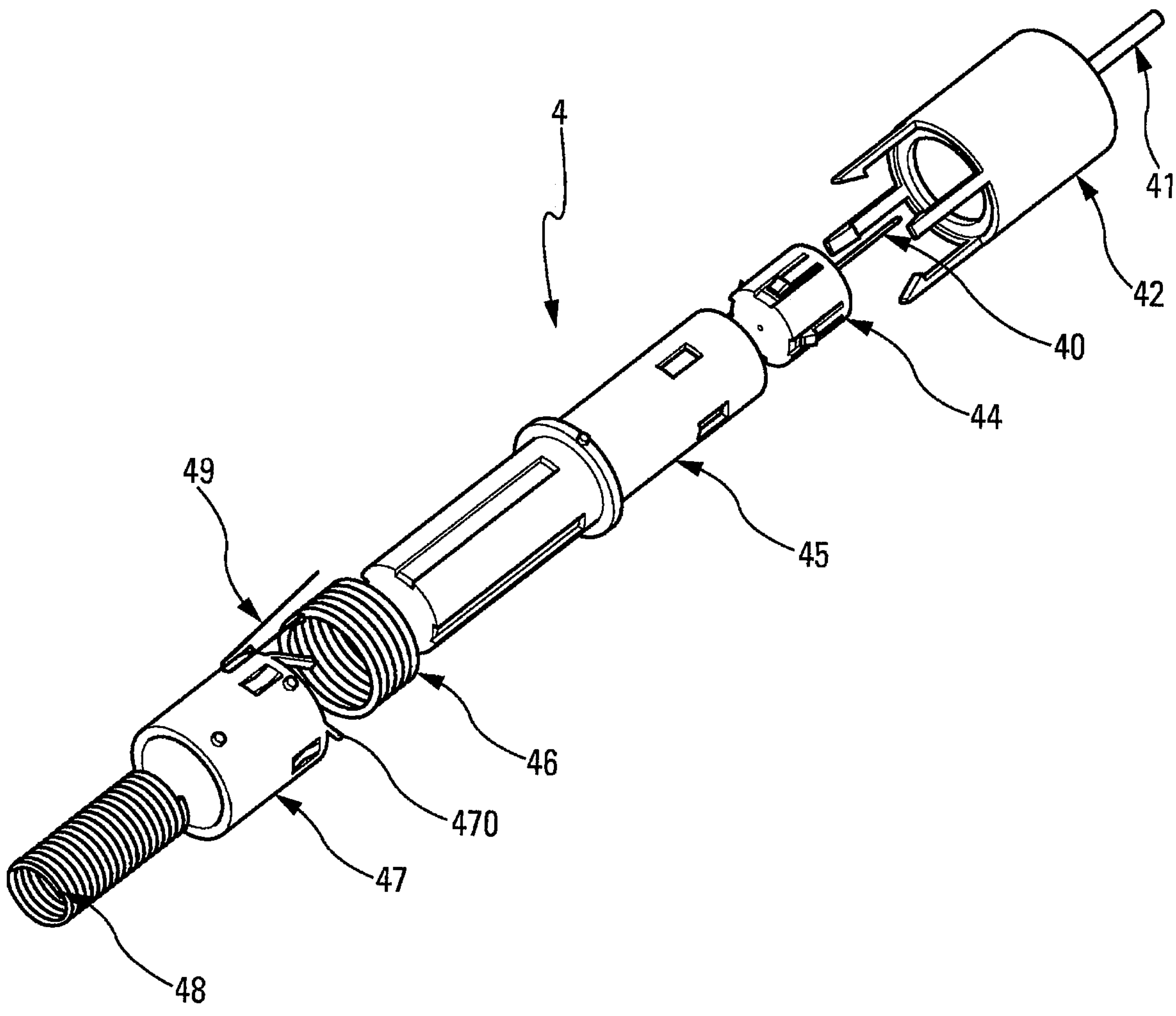
FIG. 4 is an exploded diagrammatic perspective view of a needle assembly in an advantageous embodiment.
Figure 5:
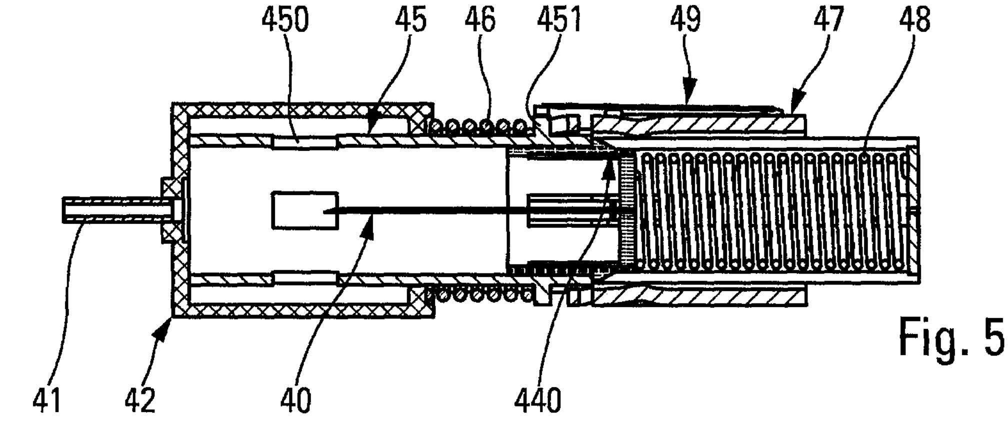
FIGS. 5 to 8 are diagrammatic side views of the actuation sequence of the FIG. 4 needle assembly.

Advantageously, before actuation, each reservoir 5 is closed by a septum-forming membrane 35, for piercing by a respective priming needle 31 during actuation, as can be seen in FIGS. 2 and 3.

The priming assembly preferably moves over a single axis of movement controlled by a linear priming actuator (not shown).

The priming actuators that are envisaged may be of any appropriate type, in particular a shape memory alloy (SMA) actuator, an electromagnetic solenoid actuator, or an electromagnetic worm gear actuator.

Actuating the device causes the following actions of the priming assembly:

1) At rest, before actuation, each priming needle 31 is closed by a respective mask 32, e.g. made of elastomer, so as to keep the priming needle 31 sterile.

2) The activation of the priming actuator causes said priming assembly 3 to advance against the membrane 35 of each reservoir 5, as shown by the arrows F in FIG. 3.

3) Each needle mask 32 is compressed against the respective reservoir 5, and deforms so as to enable the respective priming needle 3 to progress continuously through the respective membrane 35 so as to penetrate into the respective reservoir 5.

4) The priming actuator holds the priming needle 31 in position while the medication is being dispensed in any appropriate manner.

The above-described embodiment offers the following advantages in particular:

1) At rest, each priming needle 31 remains in a protected sterile environment.

2) The priming assembly 3 functions with one or more reservoirs 5; thus, if at least one priming needle 31 remains unused or does not penetrate into a respective reservoir 5, the system remains closed and functional for the remaining priming needle(s).

After the device has been primed, the injection needle 40 of the needle assembly 4 is inserted into the injection zone of the patient by means of an insertion actuator.

When a plurality of reservoirs 5 are used, as shown in the examples in FIGS. 1 to 3, the priming needles 31 of all of the reservoirs 5 are coupled to a single injection needle 40.

In addition to the injection needle 40, the needle assembly 4 advantageously comprises: a needle sleeve 41 that is optional; a retraction ring 42; a needle support 44; an insertion ring 45; a retraction spring 46; an actuator ring 47; an insertion spring 48; and an insertion actuator made of a shape memory alloy (SMA), which is made in the form of a wire 49 in this embodiment.

SMA materials, such as nickel-titanium alloy (Nitinol), are subjected to a martensitic phase transformation when they are heated. Advantageously, heating may be applied by the Joule effect. The phase transformation causes the physical dimensions of the material to change, namely a contraction of the length of the wire 49 in the embodiment described.

The typical maximum strains that may be generated in SMA wires are about 10%, and the embodiment described advantageously uses a loop in order to generate the required movement in the components described.

The SMA wire 49 returns to its previous physical state during cooling, in this embodiment obtained by natural convection after switching off the activation current. Spring elements for returning the wire to its initial shape are represented by a series of curved tabs 470 that are incorporated in the actuator ring 47.

Both the needle insertion spring 48 and the needle retraction spring 46 are in the compressed state and they are retained by respective locking means.

Activating the SMA actuator 49 by Joule effect heating in order to reach 50% of the available contraction causes the actuator ring 47 to move towards the shoulder 451 of the insertion ring 45 to which one end of the SMA actuator 49 is fastened.

In the embodiment shown, this movement causes the snap-fastener tabs 440 of the needle support 44 to deform, releasing the needle support 44 and enabling the insertion spring 48 to extend.

Extending the insertion spring 48 brings the needle support 44 and the injection needle 40 through the central bore of the insertion ring 45.

The extension of the insertion spring 48 is used to cause the injection needle 40 to penetrate into the patient, where it remains after the wire of the SMA actuator 49 has been extended.

In the embodiment shown, the movement of the needle support 44 is stopped by the snap-fastener tabs 440 engaging with cutouts 450 in the body of the insertion ring 45.

Figure 7:
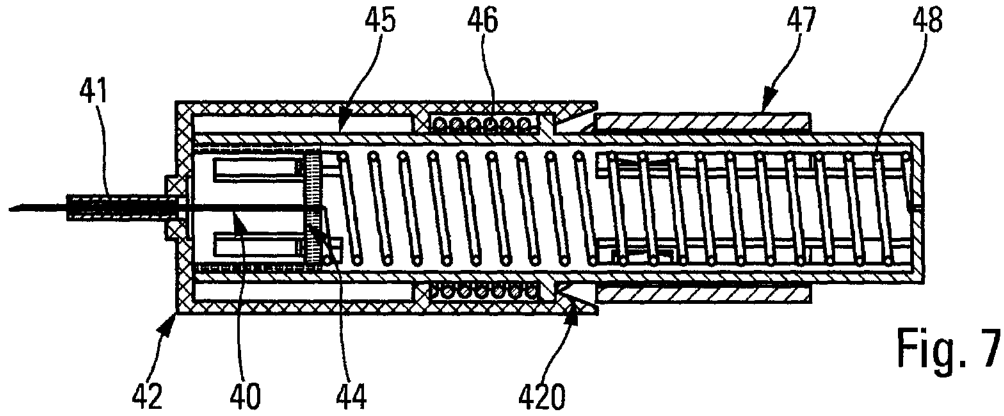
Figure 8:
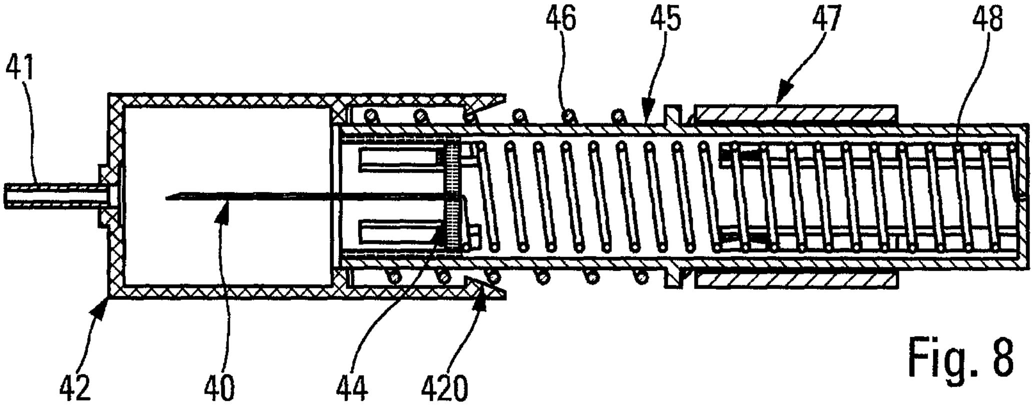
Figure 9:
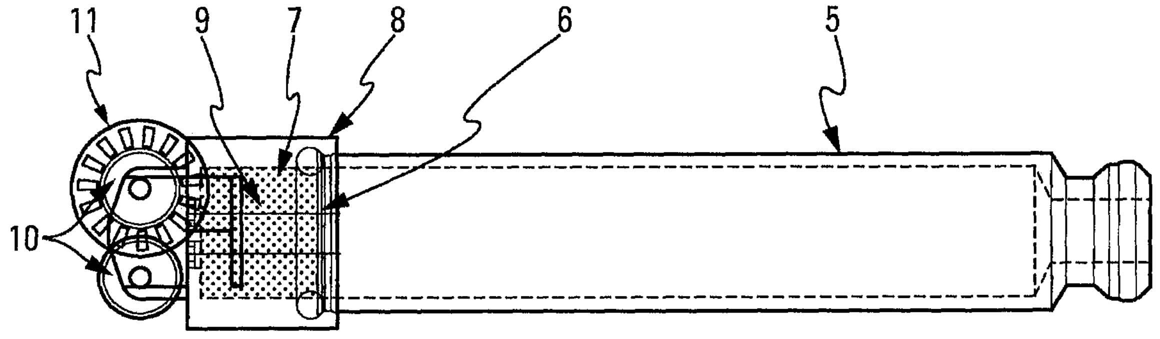
FIGS. 9 to 11 are diagrammatic side views of the actuation sequence of the FIG. 1 device.
Figure 10:
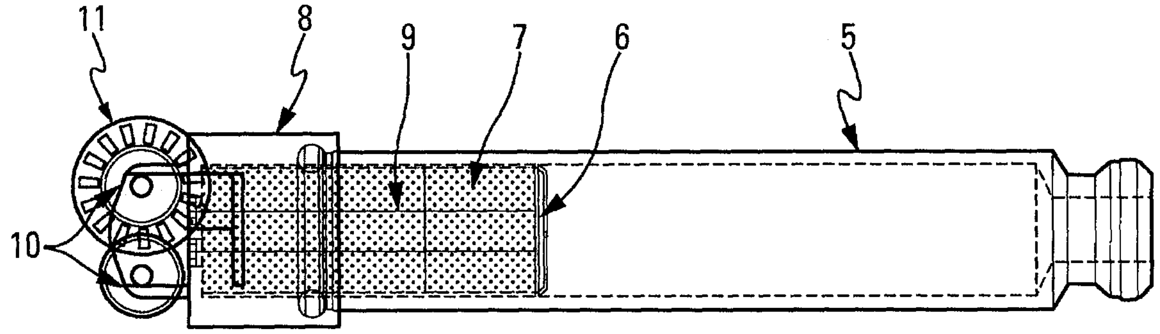
Figure 11:
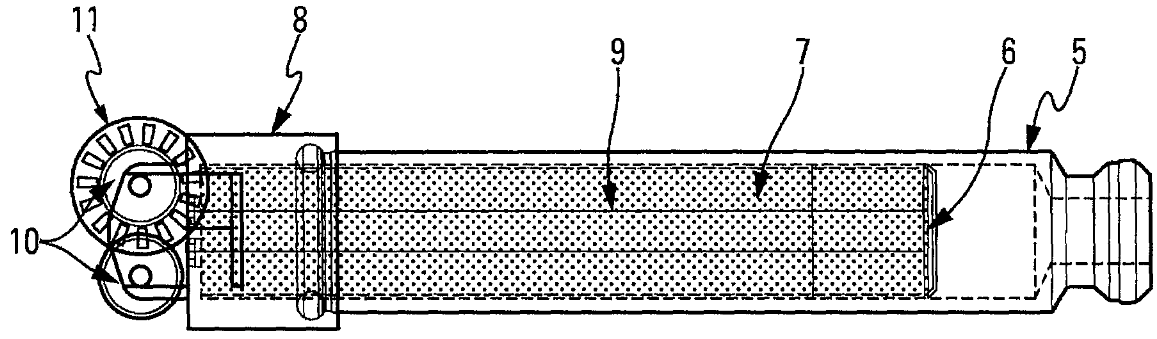

The needle insertion mechanism is shown in FIG. 7, in the inserted state of the needle.

Figure 6:
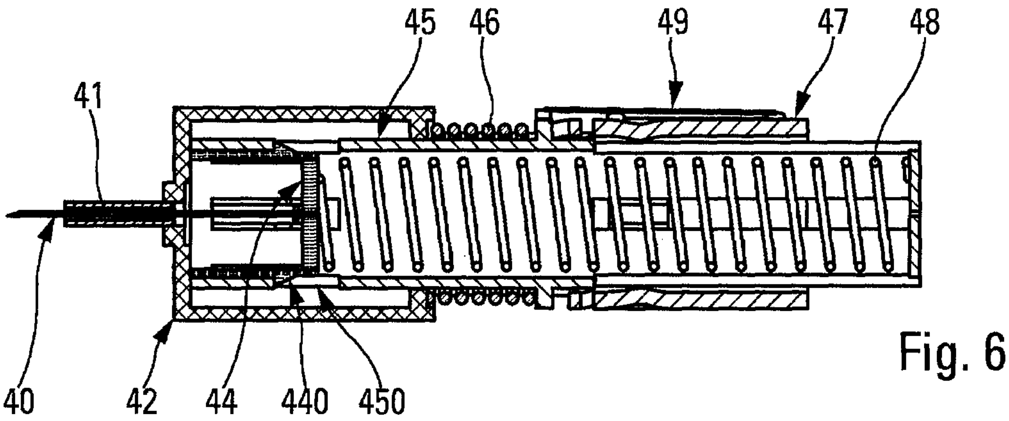

The section view of FIG. 7 is turned through 45° relative to FIG. 6 so as to show the function of the snap-fastener tabs 420 of the retraction ring 42.

Activating the SMA actuator 49 (not shown in FIG. 7) by Joule effect heating in order to reach 100% of the available contraction causes the actuator ring 47 to move towards the snap-fastener tabs 420 of the retraction ring 42.

In the embodiment shown, this movement causes the snap-fastener tabs 420 of the retraction ring 42 to deform, so as to release the insertion ring 45.

The insertion ring 45 and the interconnected assembly made up of the needle support 44 and of the injection needle 40 are entrained by the retraction spring 46 extending, being actuated by the release of the snap-fastener tabs 420.

This action retracts the needle 40 out from the user's body, and the mechanism remains in this position after the actuator wire 49 has been deactivated.

After the injection needle has been inserted, the injection mechanism is actuated.

In the embodiment shown, the injection mechanism comprises: an actuator cap 7 containing an expandable material; an actuator body 8; and heater means 9, in particular a Joule effect wire wound on a respective reel 10.

In the embodiment shown, the injection mechanism further comprises a device 11 (e.g. an optical encoder) for measuring the angular movement of at least one reel 10.

The main driver for administering fluid is the pressure created in the reservoir 5 by the expansion of the volume of the material contained in the actuator cap 7.

The operating mode may be described as follows:

1) At rest, the actuator cap 7 is held in the actuator body 8, which is fastened on the rim of the reservoir 5. The body 8 supports two reels 10 of heater wires 9 and the encoder 11. The heater wires 9 have a portion that is wound around the reel, and they also extend into the body 8 of the actuator, through the actuator cap 7, for fastening on the piston 6 of a respective reservoir 5.

2) Applying an electric current to the heater wires 9 causes them to be heated. The wires 9 are positioned with spacing sufficient to establish a uniform temperature inside the actuator, typically in the range 60° C. to 90° C. On reaching this temperature, the contents of the actuator cap 7 are subjected to significant expansion in volume.

3) Expansion of the volume of the actuator cap 7 causes the piston 6 to move along the length of the reservoir 5. The movement of the piston 6 exerts tension on the heater wires 9 that may be deployed from the reels 10 since said reels are free to turn. This mechanism further enables the actuator cap 7 to continue to expand, since the expandable material continues to be heated throughout its volume.

4) The temperature inside the actuator and the associated expansion are adjusted by controlling the electric current that is applied. This is determined by monitoring the movement of the piston as measured by means of the encoder device 11. Once sufficient fluid has been dispensed from the reservoir 5, the process is terminated by switching off the applied current.

One means for providing expansion of the volume of the actuator cap 7 as a result of a thermal stimulus is the use of thermally expandable microspheres. Thermally expandable microspheres are hollow microscopic thermoplastic spheres (having a diameter of about 12 micrometers (μm)) that encapsulate a hydrocarbon.

The encapsulated liquid is a saturated hydrocarbon that, after heating to a temperature in the range 60° C. to 90° C., expands and is subjected to a transformation into the gas phase. The encapsulation medium is a thermoplastic that softens under the heating action, making it possible for the sphere to expand in the range five times to seventy times its original volume (cf. document Y. Nishiyama, U. Nobuyuki, & C. Sato, Dismantling behavior and strength of dismantlable adhesive including thermally expandable particles, Int. J. Adhesion & Adhesives, V. 23, Iss. 5, pages 377 to 382, (2003)). Applying an external pressure of 1 megapascal (MPa) can lead to volume expanding by a total factor of 9, causing the piston to move 45 mm starting from an initial length of actuator cap 7 of 5 mm in length.

At the end of the actuator stroke, the heating is switched off. This causes the modulus of the encapsulating thermoplastic material to increase, preventing the microspheres from contracting from their expanded state. This means that the actuator stroke cannot be reused.

Encapsulated hydrocarbon microspheres are available as filler material, e.g. from the suppliers AkzoNobel (Sweden) and Matsumoto Yushi-Seiyaku Co. Ltd. (Japan).

Figure 13:
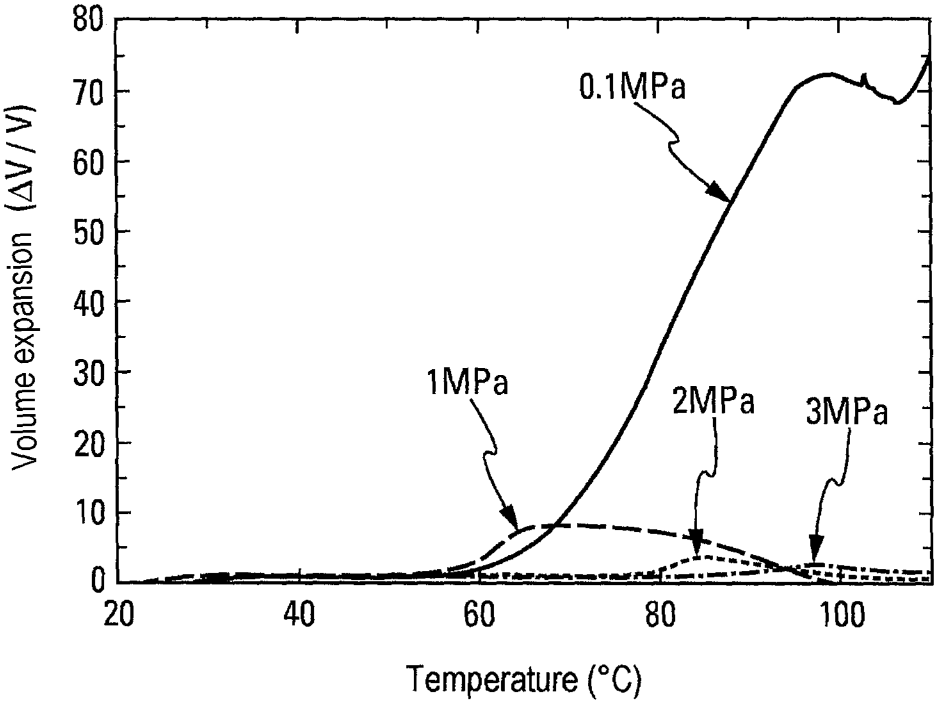
FIG. 13 is a graph showing the expansion volume of the encapsulated hydrocarbon microspheres as a function of temperature.

The table in FIG. 13 shows the volume expansion ratio of encapsulated microspheres as measured at various external pressures (source: Nishiyama et al., 2003).

Figure 12:
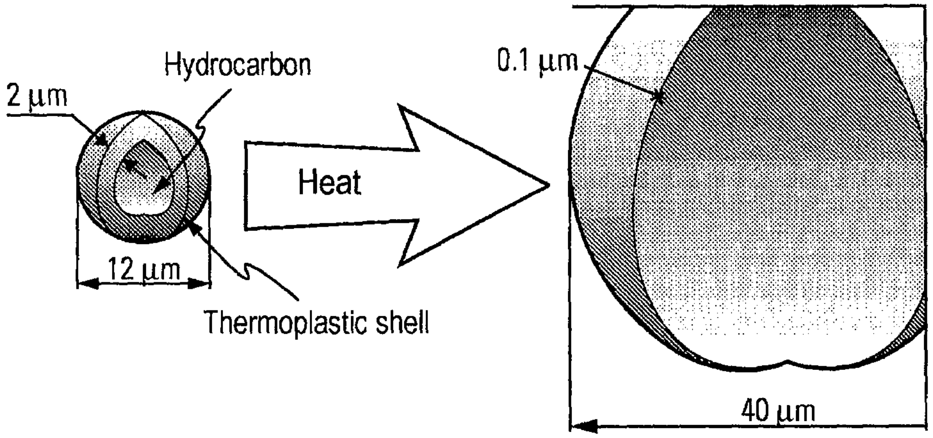
FIG. 12 is a diagram explaining the operation of the encapsulated hydrocarbon microspheres.

The diagram in FIG. 12 shows a description of the microspheres available from AkzoNobel Gamme Expancell (source: AkzoNobel, short introduction to Expancell microspheres).

Once dispensing of the fluid has terminated, the insertion actuator 8 retracts the needle into the device. The end of dispensing of the fluid can be identified by mechanical and/or software monitoring, e.g. once the drive mechanism 7 is fully extended.

The device shown in FIG. 1 includes three reservoirs 3. The three drive mechanisms may be actuated simultaneously so as to dispense the contents of the three reservoirs simultaneously, which contents are thus mixed together upstream of the injection needle 40. In a variant, the three drive mechanisms may be actuated successively so as to dispense the contents of the three reservoirs successively. Successive actuations may be triggered separately, but provision could also be made for a single actuation that automatically triggers the dispensing sequence. A combination of these two variants is also possible, e.g. dispensing in two stages, i.e. firstly dispensing the contents of one reservoir, and secondly dispensing a mixture from the other two reservoirs simultaneously.

The use of a device having multiple reservoirs makes it possible in particular to provide the following advantages:

- a single device for two or more types of fluid, which may require different volumes to be dispensed;
- the possibility of dispensing cocktails or a mixture of two or more fluids;
- the possibility of associating pain-reducing agents (anesthetics, acid neutralizers, etc.) with the medication to be injected;
- a reduction in the cost of developing devices;
- the possibility of adjusting the formulation of the fluid;
- various fluid formulations may be housed in a single device; and
- a reduction in the number of injections.

The present invention is described above with reference to an advantageous embodiment, but naturally any modification could be applied thereto by the person skilled in the art, without going beyond the ambit of the present invention, as defined by the accompanying claims.

The invention claimed is:

1. An automatic fluid injection device comprising:

a body that is fastened to a support for coming into contact with an injection zone, said body containing one or more fluid reservoirs each containing an injection piston; a needle assembly including an injection needle for penetrating into the injection zone; and an injection mechanism; said injection mechanism comprising an actuator cap containing an expandable material, and a heater for heating said expandable material, thus causing the expandable material to expand so as to move said piston in said reservoir, and thus inject a fluid into said injection zone through said injection needle, wherein said expandable material comprises thermally expandable microspheres.

2. A device according to claim 1, wherein said thermally expandable microspheres comprise hollow microscopic thermoplastic spheres encapsulating a hydrocarbon.

3. A device according to claim 2, wherein after heating said hollow microscopic thermoplastic spheres to a temperature in the range 60° C. to 90° C. said hollow microscopic thermoplastic spheres expand and are subjected to a transformation into a gas phase, so that said thermally expandable microspheres expand in a range of five times to seventy times of an original volume of said thermally expandable microspheres.

4. A device according to claim 1, including a priming assembly comprising a priming actuator and one or more priming needles for penetrating into the reservoir(s).

5. A device according to claim 1, wherein said support includes a sticker for fastening onto the injection zone.

6. A device according to claim 1, wherein each reservoir has a fluid content in the range 1 mL to 10 mL, advantageously about 3 mL.

7. A device according to claim 1, wherein said body includes a plurality of reservoirs.

8. A device according to claim 7, wherein fluids contained in said reservoirs are dispensed simultaneously, being mixed together upstream of said injection needle.

9. A device according to claim 7, wherein the fluids contained in said reservoirs are dispensed successively.

10. A device according to claim 1, including power supply.

11. A device according to claim 10, wherein the power supply is a rechargeable battery.

12. A device according to claim 10, wherein the body includes three reservoirs.

* * * * *